(12) United States Patent
Dahle

(10) Patent No.: US 8,318,478 B2
(45) Date of Patent: Nov. 27, 2012

(54) PHOTOBIOREACTOR

(75) Inventor: Lars Andreas Dahle, Stavanger (NO)

(73) Assignee: MicroA AS (NO)

( * ) Notice: Subject to any disclaimer, the term of this patent is extended or adjusted under 35 U.S.C. 154(b) by 75 days.

(21) Appl. No.: 12/830,643

(22) Filed: Jul. 6, 2010

(65) Prior Publication Data

US 2011/0165666 A1    Jul. 7, 2011

(30) Foreign Application Priority Data

Sep. 9, 2009   (NO) .................................. 20092980

(51) Int. Cl.
| | |
|---|---|
| *A01G 33/00* | (2006.01) |
| *A01G 9/00* | (2006.01) |
| *C12M 1/00* | (2006.01) |
| *C12M 3/00* | (2006.01) |
| *F21V 33/00* | (2006.01) |
| *A01K 63/04* | (2006.01) |

(52) U.S. Cl. ............ 435/292.1; 47/1.4; 47/17; 362/101; 119/226

(58) Field of Classification Search ............... 435/292.1, 435/292.2, 292.3; 47/1.4, 17; 119/226; 362/101
See application file for complete search history.

(56) References Cited

U.S. PATENT DOCUMENTS

| 3,955,317 A | 5/1976 | Gudin |
|---|---|---|
| 5,534,417 A | 7/1996 | Arad et al. |
| 5,981,271 A | 11/1999 | Doucha et al. |
| 2008/0274494 A1 | 11/2008 | Kertz |
| 2009/0130706 A1* | 5/2009 | Berzin et al. .................... 435/41 |

FOREIGN PATENT DOCUMENTS

| CN | 101709264 A | 5/2010 |
|---|---|---|
| GB | 2118572 A | 11/1983 |
| IT | F950093 | 6/1973 |
| IT | FI2009A000167 A1 | 7/2009 |
| WO | 2004/074423 A2 | 9/2004 |
| WO | 2005121309 A1 | 12/2005 |
| WO | WO 2005121309 A1 * | 12/2005 |
| WO | 2007/098150 A2 | 8/2007 |
| WO | WO 2007098150 A2 * | 8/2007 |
| WO | 2008010737 A1 | 1/2008 |
| WO | 2009/153790 A1 | 12/2009 |
| WO | 2010/076795 A1 | 7/2010 |
| WO | 2011/013104 A1 | 2/2011 |

OTHER PUBLICATIONS

Carlozzi and Torzillo, 1996, (Productivity of Spirulina in a strongly curved outdoor tubular photobioreactor. Appl. Microbiol. Biotechnol., 45:18-23).

* cited by examiner

*Primary Examiner* — Nathan Bowers
*Assistant Examiner* — Lydia Edwards
(74) *Attorney, Agent, or Firm* — Andrus, Sceales, Starke & Sawall, LLP

(57) ABSTRACT

A photobioreactor comprising a receptacle with a first and a second outer side surface, wherein the receptacle is formed from a flexible, fluid-tight and transparent material, and wherein the receptacle is disposed in a rack provided with elongated, substantially vertical, support elements arranged in at least one horizontal row, whereby the support elements abut, in an alternating and supporting manner, against the first and the second outer side surfaces of the receptacle.

24 Claims, 4 Drawing Sheets

PHOTOBIOREACTOR

CROSS-REFERENCE TO RELATED APPLICATION

This application claims priority of Norwegian Patent Application No. 20092980, filed Sep. 9, 2009, which application is incorporated herein by reference.

BACKGROUND

This disclosure relates to a photobioreactor for cultivating photosynthetic microorganisms. More particularly, this disclosure relates to a photobioreactor for photosynthetic organisms, in which the photobioreactor combines a large reactor volume with a short light path, which provides a large yield when photosynthetic microorganisms are cultivated.

A number of species of photosynthetic or phototrophic microorganisms, especially algae, are cultivated commercially. Photosynthetic microorganisms comprise a number of species, for example, but not limited to, *Spirulina* spp., *Chlorella* spp., *Arthrospira* spp., *Dunaliella* spp. and cyanobacteria.

Microalgae may be used as a food supplement given that they contain long-chained, polyunsaturated fatty acids, vitamins and antioxidants. They may also be used in the pharmaceutical industry given that some species contain pharmaceutically active substances, such as sterols, antimicrobial substances, antiviral substances and cancer-treating substances.

Photosynthetic microorganisms may also be used for energy production. By means of solar energy, green algae and cyanobacteria can decompose water into hydrogen and oxygen. Algae may be used as a source of biodiesel and are far more efficient for this purpose than that of traditional oil plants, for example oil palms.

Photosynthetic microorganisms are dependent on light as their energy source, $CO_2$ dissolved in water as their carbon source, and nutrient salts in water as their source of mainly nitrogen, potassium, phosphorous and sulphur, and also trace minerals, for example iron, calcium, and magnesium.

Photosynthetic microorganisms may be cultivated indoors by means of artificial light, but most commonly the algae are cultivated outdoors in sunlight. The productivity, which is measured as biomass per unit of volume, depends on the availability of light and the light regime, among other things. The light regime refers to the time ratio between light and darkness.

There are a number of systems for cultivating microalgae. A simple cultivation method having low investment costs involves use of shallow ponds. A disadvantage of these ponds is that the microorganisms at the surface receive much light, whereas cells located a few centimetres further down in the water column receive less light. When the culture becomes dense, cells further down in the water column will receive very little light. They will therefore not grow. This may be remedied to a certain degree by stirring the water, insofar as turbulence will allow more cells to become exposed to sunlight.

Other systems for cultivating microalgae comprise pipe systems, formed either from straight pipes or curved pipes, as disclosed in patent documents ITF950093, WO 2008010737, GB 2118572 and U.S. Pat. No. 3,955,317, and by e.g. Carlozzi and Torzillo, 1996, (Productivity of *Spirulina* in a strongly curved outdoor tubular photobioreactor. Appl. Microbiol. Biotechnol., 45:18-23). A disadvantage of pipe systems is that the volume within the photobioreactor is relatively small relative to the floorage or the area required by the system for the installation thereof, the so-called footprint. The pipe diameter must be kept relatively small in order for the light to reach the microorganisms in the part of the pipe located farthest away from the light source. Another disadvantage is that the flow in a pipe system is laminar. This may be remedied somewhat by means of curved pipes, in which the flow will be more turbulent.

Patent document US 2008274494 discloses a photobioreactor made of a transparent, flexible polymer material, for example polyethylene. The photobioreactor is suspended downwards from a rack in the form of a long, relatively wide and thin bag. Further, the bag is provided with internal flow deflectors in order to create turbulence when the algae cultivation medium flows down through the bag. The internal flow deflectors will also keep the walls of the bag together, whereby the bag does not bulge when being filled with liquid. The applicant's own patent document WO 2005121309 discloses a photobioreactor in the form of a flat, suspended bag with channels formed in the bag. Patent document U.S. Pat. No. 5,534,417 discloses a photobioreactor consisting of a series of pipes suspended downwards from a rack.

Patent document U.S. Pat. No. 5,981,271 discloses an apparatus for cultivating algae outdoors, wherein the algae reactor is a flat-lying chamber with a drop of approximately 3%. The depth of the chamber is approximately 5 cm.

Hereinafter, a cultivation fluid implies a liquid composed of components selected from the group consisting of: freshwater, brackish water, sea water, salt solution, bacteria, phototrophic bacteria, cyanobacteria, unicellular eukaryotic algae, multicellular eukaryotic algae, dinoflagellates, euglena, nutrient salts, gases in dissolved form, gases in non-dissolved form, minerals, trace elements, vitamins, acidity regulators, chelators, surfactants, antibiotics and thickeners.

SUMMARY

In a first aspect, this disclosure relates to a photobioreactor comprising a receptacle with a first and a second outer side surface, wherein the receptacle is formed from a flexible, fluid-tight and transparent material, and wherein the receptacle is disposed in a rack provided with elongated, substantially vertical, support elements arranged in at least one horizontal row, whereby the support elements abut, in an alternating and supporting manner, against the first and the second outer side surfaces of the receptacle. The advantage thereof is that when filling the receptacle with cultivation liquid, it will distend and be forced against the support elements due to the liquid pressure. The support elements will cause the receptacle, when in position of use, to assume a relatively flat shape in the vertical direction, and an elongated shape in the horizontal direction. By so doing, advantages over the prior art are achieved by virtue of forming a relatively short light path between the first and the second side surface of the receptacle whilst simultaneously allowing the receptacle to hold a relatively large volume of cultivation liquid.

The photobioreactor may be provided with a frame which may be comprised of at least one element selected from the group consisting of a lower frame element, an upper frame element, a side frame element and a tensioning element.

The distance between two consecutive support elements may be substantially smaller than the vertical extent of the receptacle when in position of use. For example, the distance may be 5 cm, alternatively 10 cm, alternatively 15 cm and further alternatively 20 cm. The support elements may be arranged in two rows. In one embodiment, the support elements in a first row may be offset horizontally relative to the support elements in a second row.

In one embodiment, at least every other support element may be movably associated with the frame in a direction perpendicular to a centre line. In a further embodiment, to at least every other support element may be eccentrically rotatable about a vertical longitudinal axis of the support element. These two embodiments allow the distance between the first and the second side surface of the receptacle to be adjusted.

The support elements, at lower end portions thereof, may be fixed to a lower frame element. Further, the support elements, at upper end portions thereof, may be fixed to an upper frame element.

The receptacle, at a first end portion and a second end portion thereof, may be provided with a respective first and second tensioning element fixed to at least a lower frame element of the rack.

The upper frame element may be provided with means for positioning the receptacle in the vertical direction. The upper frame element may be provided with at least two suspension mechanisms, and each suspension mechanism may be comprised of at least two ball transfer units with balls, the free portion of the balls forming substantially a vertical gap. The receptacle, along an upper edge thereof when in position of use, may be provided with means for positioning the receptacle in the vertical direction. The receptacle, along the upper edge thereof when in position of use, may be provided with a longitudinal thickening. The longitudinal thickening may be comprised of a wire. The advantage thereof is that an empty receptacle may be positioned quickly in the rack in the desired vertical position along the entire length of the receptacle before filling cultivation liquid into the receptacle.

BRIEF DESCRIPTION OF THE DRAWINGS

Hereinafter, an example of preferred embodiments is described and is depicted in the accompanying drawings, where.

DETAILED DESCRIPTION OF THE DRAWINGS

Figure 1:
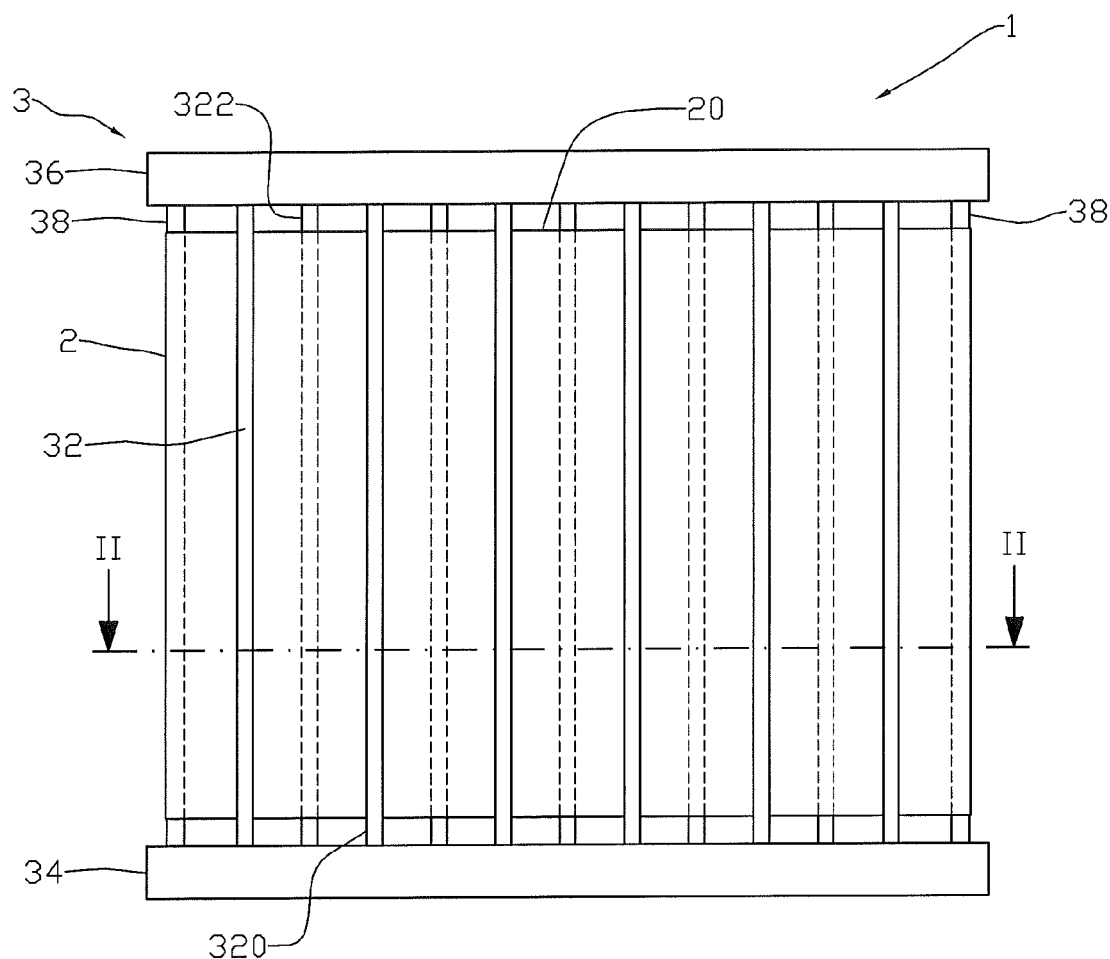
FIG. 1 schematically shows a photobioreactor in side view.

In the drawings, reference numeral 1 indicates a photobioreactor. The photobioreactor 1 comprises a receptacle 2 provided with a first outer side surface 20 and a second outer side surface 20'. The receptacle 2 is formed from a flexible, fluid-tight and transparent material, for example a plastics material. The receptacle 2 may be formed like a sausage, or it may be formed by laying a first plastic foil over a second plastic foil and then joining the plastic foils at their side edges, for example by welding. The width of the receptacle 2 may be adapted to its use and may be, for example, 0.75 m, 1 m, 1.5 m, 2 m or more than 2 m. The length of the receptacle 2 is chosen relative to the desired volume of the receptacle 2 and, beyond this, there are no other limitations than limitations of a practical nature. For example, the length may be 5 m, 10 m, 25 m, 50 m, 75 m, 100 m or longer than 100 m.

The receptacle 2 is disposed in a rack 3. The rack 3 is provided with elongated, substantially vertical, support elements 32, which are shown arranged in two rows in the figures, with the exception of FIG. 2d. In an alternative embodiment, the support elements 32 may be arranged in one row, as shown in FIG. 2d. The support elements 32, at lower portions 320 thereof, are fixed to a lower frame element 34 and, at upper portions 322 thereof, they are fixed to an upper frame element 36. The lower frame element 34 and the upper frame element 36 are provided with means (not shown) for sideways support, and means (not shown) for fixing the upper frame element 36 to the upper portions 322 of the support elements. The lower frame element 34 may rest on a ground, for example a floor or a field. In an alternative embodiment, the lower frame element 34 may be comprised of holes in a floor or holes in the ground.

The receptacle 2, at a first end portion 22 thereof, is provided with a tensioning element 38 and, at a second end portion 24 thereof, is provided with a corresponding tensioning element 38. The receptacle 2, at the end portions 22, 24 thereof, may be fixed to the tensioning element 38 by having positioned the receptacle 2 around the tensioning element 38, as shown in FIGS. 2a-d, and by having attached the receptacle 2 to itself, in an overlapping manner, by means of a weld seam 26.

The horizontal distance between the outer side surfaces 20, 20' of the receptacle 2 depends on two factors: the horizontal distance between two consecutive support elements 32; and the distance between the sides of the support element 32, which abut, in a supporting manner, against the receptacle 2, and the centre line 4 of the photobioreactor 1, as depicted in FIGS. 2a-d. Advantageously, practical tests have shown that the horizontal distance between two consecutive support elements 32 may be between 5 and 20 cm, however not limited thereto.

Figure 2A:
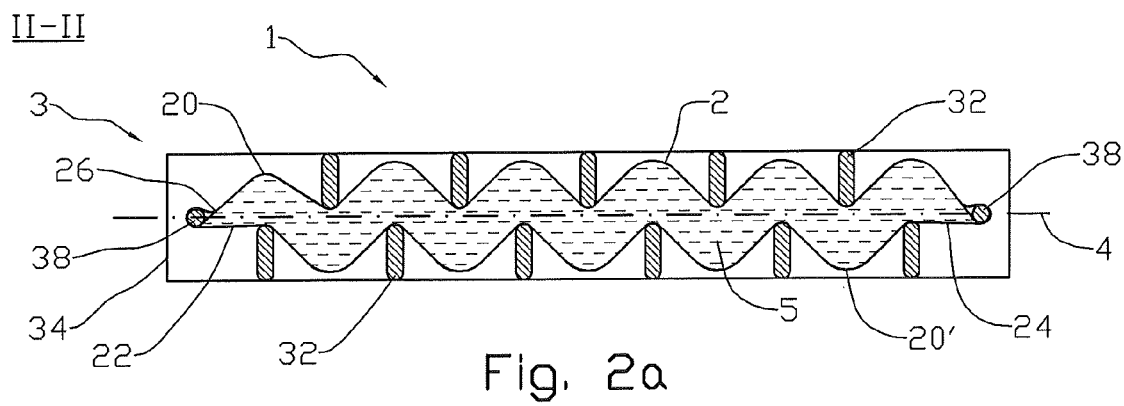
FIGS. 2a-d schematically show a photobioreactor as viewed from above along section II-II of FIG. 1, wherein the positioning of the support elements is shown at different positions and with different cross-sectional designs.
Figure 2B:
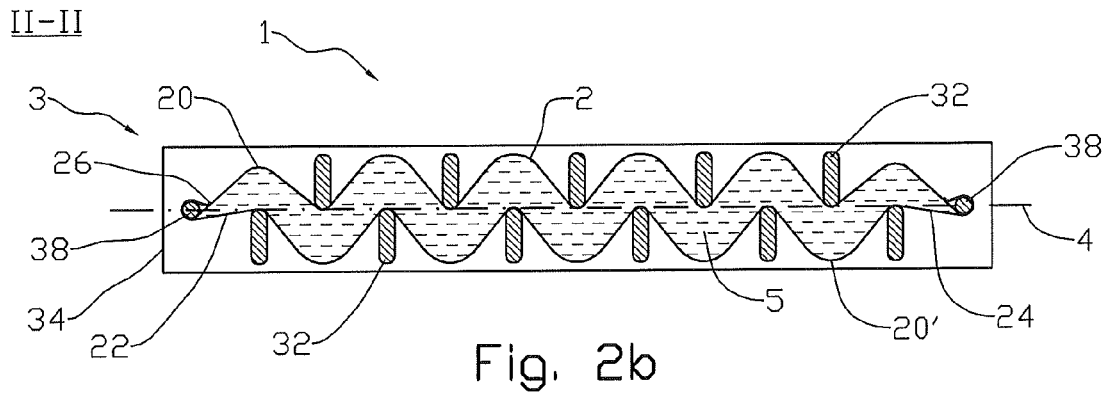
Figure 2C:
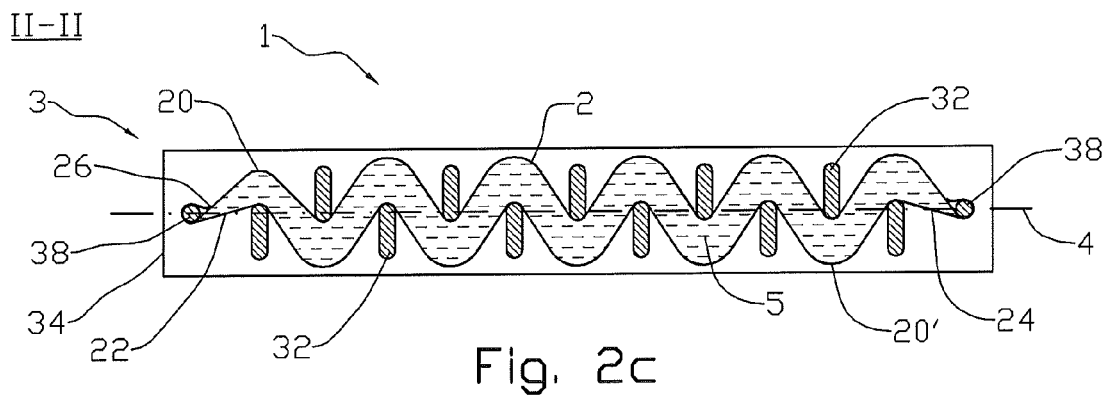
Figure 2D:
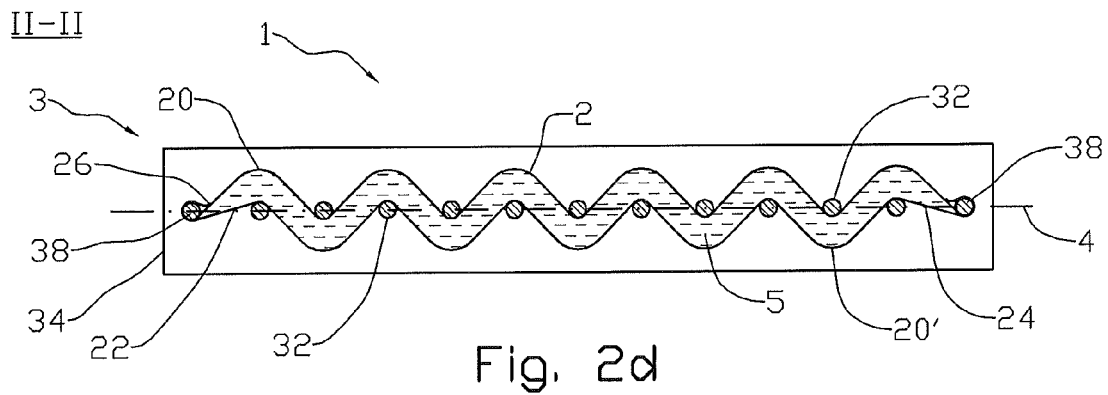
Figure 3A:
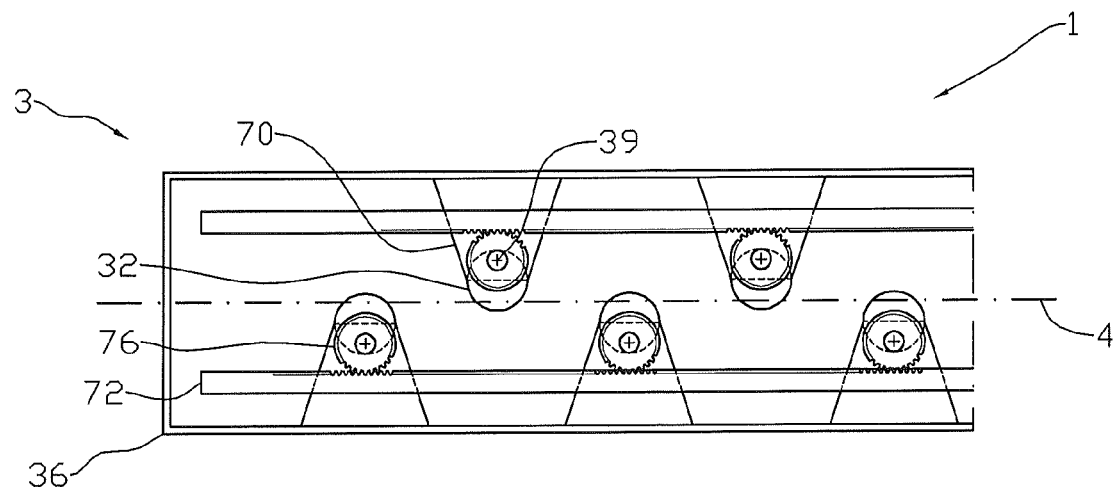
FIGS. 3a-b show, in larger scale, an alternative embodiment of support elements having an eccentric mounting to the frame of the photobioreactor.
Figure 3B:
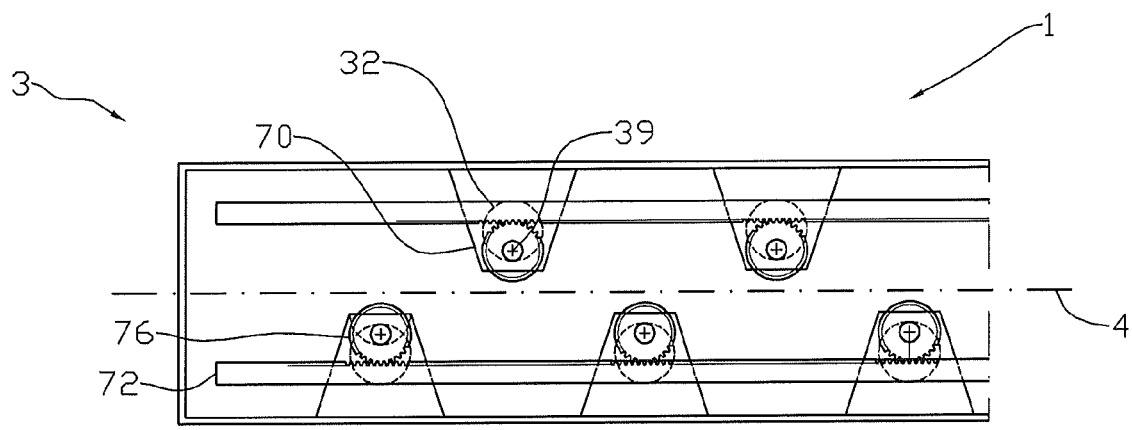

The support element 32 may be formed with an oblong cross section, as shown in FIGS. 2a-c, or with a circular cross section, as shown in FIGS. 2d and 3a-b. Advantageously, the cross section of the support element 32 may be rounded on the side abutting, in a supporting manner, against the receptacle 2. Support elements 32 formed with an oblong cross section and having the longer axis of the cross section placed perpendicular to the centre line 4 of the photobioreactor 1, as shown in FIGS. 2a-c, will exhibit a considerable flexural rigidity when the receptacle 2 is filled with cultivation liquid 5.

The support elements 32 may be arranged in one row or two rows, as shown in FIGS. 2a-d and 3a-b. The two rows may be substantially parallel. When the support elements 32 are arranged in two rows, the sides of the support elements 32 abutting, in a supporting manner, against the receptacle 2 may be located substantially on the centre line 4, as shown in FIG. 2b. In an alternative embodiment, which is shown in FIG. 2a, the sides of the support elements 32 abutting, in a supporting manner, against the receptacle 2 have been moved outside the centre line 4. In a further, alternative embodiment, which is shown in FIG. 2c, the sides of the support elements 32 abutting, in a supporting manner, against the receptacle 2 have been moved inside the centre line 4.

In an alternative embodiment, the support elements 32 may be movably arranged in a direction perpendicular to the centre line 4. In a first position, the support elements 32 may have been moved so as to assume a position as shown in FIG. 2a. In a second position, the support elements 32 may have been moved so as to assume a position as shown in FIG. 2b; in a third position, the support elements 32 may have been moved so as to assume a position as shown in FIG. 2c; and in a fourth position, the support elements 32 may have been moved so as to assume a position corresponding to the position shown in FIG. 2d. The support elements 32 may also be moved into positions located between these indicated positions. It is obvious that such arrangements of the support elements 32 may be achieved by virtue of every other support element 32 being fixedly arranged in the rack 3, and by virtue of the complementary support elements 32 being movable in a direction perpendicular to the centre line 4. In context of such an arrangement, the centre line 4 will move along with the movement of the complementary support elements 32.

In a further, alternative embodiment, as shown in FIGS. 3a and 3b, the support elements 32 may be eccentrically supported about an axis 39 in the lower frame element 34, and to a mounting bracket 70 fixed to the upper frame element 36. The support elements 32 are rotated into the desired position using means known per se, which may comprise the mounting bracket 70, an adjustment rod 72 provided with a toothing 74 and a toothed wheel 76. The toothed wheel 76 may be connected to the support element 32 via an axle (not shown) extending from the end portion 322 of the support element 32 (see FIG. 1) along the extension of the eccentric longitudinal axis 39 of the support element 32 through a recess (not shown) in the mounting bracket 70 onto the centre of the toothed wheel 76. FIG. 3a shows the support elements 32 rotated, by means of the adjustment rods 72, into a position within which a portion of the support elements 32 are located inside the centre line 4. FIG. 3b shows the support elements 32 rotated into a position within which the support elements 32 face away from the centre line 4. A receptacle 2, which is placed in the photobioreactor 1, as shown in FIG. 3a, will assume a shape approximating the shape shown in FIG. 2c, whereas a receptacle 2, which is placed in the photobioreactor 1, as shown in FIG. 3b, will assume a shape approximating the shape shown in FIG. 2a. The person skilled in the art will know that the support elements 32 may have a cross section different from a circular cross section. For example, the cross section may be cam-shaped. Further, it is obvious that every other support element 32 may be rotatable about an axis 39, whereas the complementary support elements 32 are fixed. It is also obvious for the feature of rotatable support elements 32 to be combined with complementary support elements 32 being movable in a direction perpendicular to the centre line 4. The rotatable support elements 32 may also be arranged to be movable perpendicular to the centre line 4.

In an alternative embodiment, the support elements 32 may be releasably attached to the lower frame element 34 and the upper frame element 36. This is advantageous when placing the receptacle 2 in the rack 3. Before placement of the receptacle 2, all the support elements 32 are lifted out of the lower frame element 34 and the upper frame element 36 via recesses extending through the upper frame element 36 (not shown). The tensioning element 38 of the first end portion 22 of the receptacle 2 is fixed to the rack 3. The receptacle 2 is introduced between the lower frame element 34 and upper frame element 36. The support elements 32 are put into place consecutively by inserting them through the recesses in the upper frame element 36 and down into a complementary recesses in the lower frame element (not shown), and in such a way that the support elements 32 abut, in alternating and supporting manner, against the first and the second side surfaces 20, 20' of the receptacle 2. Finally, the second end portion 24 of the receptacle 2 is fixed to the rack 3 by means of the tensioning element 38.

In an alternative embodiment, the support elements 32 may be supported, in a centrically rotatable manner (not shown), to the lower frame element 34 and the upper frame element 36. The first end portion 22 of the receptacle 2 is passed between the support elements 32 in so as to allow the support elements 32 to abut, in an alternating and supporting manner, against the first and the second side surfaces 20, 22' of the receptacle 2. This provides the advantage of allowing the receptacle 2 to be passed through the rack 3 without experiencing substantial friction from the support elements when forming either one row or having a portion located inside the centre line 4.

In a further, alternative embodiment, the attachment of the support element 32 to the lower frame element 34 is sufficiently strong to render the upper frame element 36 superfluous. The receptacle 2 is carried forward between the support elements 32 and is held tightly by the tensioning elements 38, which are attached to the lower frame element 34, and it is fixed to the upper portion of the tensioning elements 38 using, for example, a rope (not shown).

Figure 4:
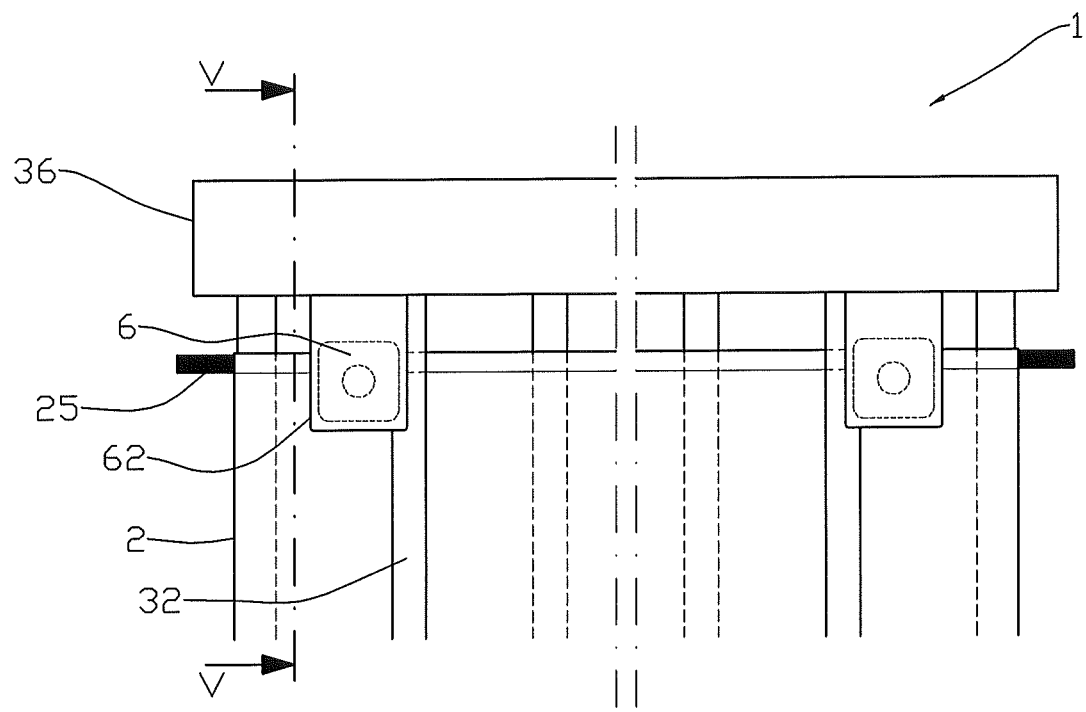
FIG. 4 shows, in yet another scale, a simplified longitudinal view of a photobioreactor with suspension devices for a receptacle.
Figure 5:
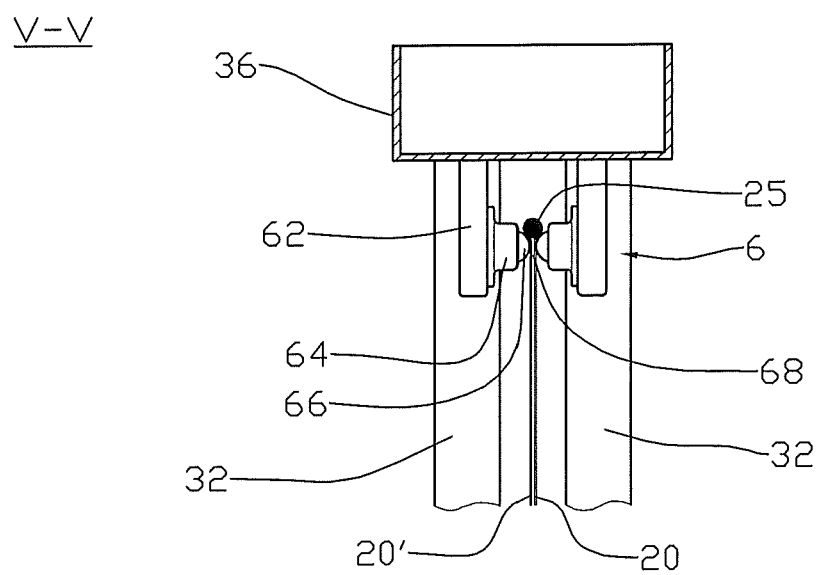
FIG. 5 shows a simplified cross-sectional view along the section V-V of FIG. 4 of a photobioreactor with suspension devices for a receptacle.

When the receptacle 2 is filled with cultivation liquid 5, the cultivation liquid 5 will exert a pressure against the side surfaces 20, 20' of the receptacle 2. This pressure will generate a corresponding counter-pressure, from the support elements 32, directed towards the outer side surfaces 20, 20' of the receptacle. The friction between the support elements 32 and the side surfaces 20, 20' of the receptacle 2 cause the receptacle 2 to maintain its vertical position and not to sag down along the support elements 32. The vertical position may also be maintained by filling the receptacle with a gas, for example air, and then filling the receptacle with cultivation fluid 5. Before filling the receptacle 2 with gas or cultivation fluid 5, it must be placed in the desired, vertical position between the support elements 32 and be kept in this position. In one embodiment, this may be done as shown in FIGS. 4 and 5. The receptacle 2 is provided with a wire 25 or some other thickening at the longitudinal edge of the receptacle 2, the edge of which is located uppermost when the receptacle 2 is placed in its position of use. The rack 3 is provided with a suspension mechanism 6 at suitable intervals. The suspension mechanism 6 is comprised of a housing 62 fixed to the upper frame element 36 in a manner known per se, and along the centre line 4. The housing 62 is provided with at least two so-called ball transfer units 64 with bails 66 of a type known per se, the free portions of the bails 66 facing each other and forming generally a vertical gap 68 extending substantially along the centre line 4. The vertical gap 68 is sufficiently wide for the receptacle 2 to be passed through the housing 62 and between the free end portions of the balls 66, however being sufficiently narrow for the wire 25 to rest on the balls 66 without allowing it to be pulled vertically down through the gap 68. The result of so doing is that the receptacle 2 may be moved readily along the centre line 4 of the photobioreactor 1 and be kept in a vertical position of use until having filled the receptacle 2 with cultivation liquid 5. In an alternative embodiment, the upper frame element 36, at the underside thereof, is provided with a glide rail (not shown). Examples of such glide rails are curtain rails or rails known from sailing boats, the rail of which is attached to the mast to facilitate the hoisting and lowering of sails. In this embodiment, the receptacle 2, at the upper edge thereof, is provided with suitable intervals having gliders complementarily fitting the profile of the rail (not shown).

Viewed from above, the photobioreactor 1 may have different shapes. It may form a generally straight line, it may be curved, or the photobioreactor 1 may form a general U shape (not shown), which causes the first end portion 22 and the second end portion 24 of the photobioreactor 1 to be located in vicinity of each other. This presents advantages during the operation of the photobioreactor 1 owing to the fact that required connections, such as lines for filling of liquid and draining of liquid, lines for supply of air and/or $CO_2$ gas, lines for draining of gas, and lines for harvesting from the photobioreactor 1, advantageously are connected to the end portions 22 and 24 of the photobioreactor 1. Such lines for operation of the photobioreactor 1, and the manner in which they are to be connected to the photobioreactor 1, are known to the person skilled in the art and are not described in detail herein. Moreover, they are not shown in the drawings. Bringing the end portions 22, 24 of the photobioreactor 1 in vicinity of each other allows equipment for operation of the photobioreactor 1 to be concentrated within an operational centre (not shown). Several photobioreactors 1 may be connected to the same operational centre.

In a photobioreactor 1 of this type it is essential that there is a supply of especially gas containing $CO_2$ along the entire length of the photobioreactor 1. Therefore, the receptacle 2 is provided with a perforated hose at the lower part thereof. This hose may be of a type known per se, for example a diffuser hose (not shown). The diffuser hose may be disposed between two layers of plastic foil before being welded along their longitudinal edges to a receptacle 2, as described above. In cases where the receptacle 2 is formed as a pipe, the diffuser hose may be moved through the receptacle in several ways. For example, a metal piece made of iron may be releasably attached to the end portion of the diffuser hose. By moving a powerful magnet on the outside of the receptacle 2, the diffuser hose may be moved through the receptacle 2. Correspondingly, a strong magnet may be releasably attached to the diffuser hose, and a piece made of iron may be moved on the outside of the receptacle 2. Upon using particularly long receptacles 2, the diffuser hose will be too heavy for allowing said methods to be used. An alternative method may be to attach a metal piece or a magnet to an end portion of a thin line and move the line through the receptacle 2, after which the line is releasably attached to the diffuser hose and the diffuser hose is pulled through the receptacle 2 by means of the line.

The diffuser hose may be formed from a heavy material in order to prevent the diffuser hose from floating up in the cultivation liquid 5. In an alternative embodiment, the diffuser hose may be provided with weights in order to resist buoyancy. In yet another embodiment, the diffuser hose may be fixed to the receptacle 2.

The invention claimed is:

1. A photobioreactor comprising a receptacle with a first and a second outer side surface, wherein the receptacle is formed from a flexible, fluid-tight and transparent material, wherein the receptacle is disposed in a rack provided with a plurality of elongated, substantially vertical, support elements arranged in at least one row extending along a center line, each support element being spaced apart from the other support elements in the plurality with respect to the center line, and wherein the support elements abut, in an alternating and supporting manner along the center line, against the first and then the second outer side surfaces of the receptacle.

2. The photobioreactor in accordance with claim 1, comprising a tensioning element located at an end portion of the receptacle and tensioning the receptacle with respect to the center line.

3. The photobioreactor in accordance with claim 1, wherein the distance between two consecutive support elements in the plurality is substantially smaller than the vertical extent of the receptacle when in position of use.

4. The photobioreactor in accordance with claim 1, wherein the support elements are arranged in two rows.

5. The photobioreactor in accordance with claim 1, wherein the support elements, at lower end portions thereof, are fixed to a lower frame element.

6. The photobioreactor in accordance with claim 1, wherein the support elements, at upper end portions thereof, are fixed to an upper frame element.

7. The photobioreactor in accordance with claim 1, wherein the receptacle, at a first end portion and a second end portion thereof, is provided with a respective first and second tensioning element fixed to at least a lower frame element of the rack.

8. The photobioreactor in accordance with claim 1, wherein an upper frame element is provided with means for positioning the receptacle in the vertical direction.

9. The photobioreactor in accordance with claim 1, wherein the receptacle, along an upper edge thereof when in position of use, is provided with means for positioning the receptacle in the vertical direction.

10. The photobioreactor in accordance with claim 1, wherein the plurality of support elements are arranged in a single row.

11. The photobioreactor in accordance with claim 1, wherein the plurality of support elements are arranged in two rows located on opposite sides of the center line, respectively.

12. The photobioreactor in accordance with claim 11, wherein sides of the support elements that abut the receptacle are located on the center line.

13. The photobioreactor in accordance with claim 11, wherein sides of the support elements that abut the receptacle are spaced apart from the center line.

14. The photobioreactor in accordance with claim 13, wherein the support elements are located on the center line.

15. The photobioreactor in accordance with claim 13, wherein the support elements are spaced apart from the center line.

16. The photobioreactor in accordance with claim 1, wherein the center line is straight.

17. A photobioreactor comprising a receptacle with a first and a second outer side surface, wherein the receptacle is formed from a flexible, fluid-tight and transparent material, wherein the receptacle is disposed in a rack provided with elongated, substantially vertical, support elements arranged in at least one horizontal row, whereby the support elements abut, in an alternating and supporting manner, against the first and the second outer side surfaces of the receptacle; wherein the support elements are arranged in two rows; wherein the support elements in a first row are offset horizontally relative to the support elements in a second row.

18. A photobioreactor comprising a receptacle with a first and a second outer side surface, wherein the receptacle is formed from a flexible, fluid-tight and transparent material, wherein the receptacle is disposed in a rack provided with elongated, substantially vertical, support elements arranged in at least one horizontal row, whereby the support elements abut, in an alternating and supporting manner, against the first and the second outer side surfaces of the receptacle; wherein at least every other support element is movably positionable with respect to the frame in a direction perpendicular to a center line.

19. A photobioreactor comprising a receptacle with a first and a second outer side surface, wherein the receptacle is formed from a flexible, fluid-tight and transparent material, wherein the receptacle is disposed in a rack provided with elongated, substantially vertical, support elements arranged in at least one horizontal row, whereby the support elements abut, in an alternating and supporting manner, against the first and the second outer side surfaces of the receptacle; wherein at least every other support element is rotatable with respect to a vertical longitudinal axis of the support element towards and away from the center line.

20. A photobioreactor comprising a receptacle with a first and a second outer side surface, wherein the receptacle is formed from a flexible, fluid-tight and transparent material, wherein the receptacle is disposed in a rack provided with elongated, substantially vertical, support elements arranged in at least one horizontal row, whereby the support elements abut, in an alternating and supporting manner, against the first and the second outer side surfaces of the receptacle; wherein an upper frame element is provided with means for positioning the receptacle in the vertical direction; wherein the upper frame element is provided with at least two suspension mechanisms, and each suspension mechanism is comprised of at least two ball transfer units with balls, the free portion of the balls forming substantially a vertical gap.

21. The photobioreactor in accordance with claim 20, wherein the receptacle, along an upper edge thereof when in position of use, is provided with a longitudinal thickening.

22. The photobioreactor in accordance with claim 21, wherein the longitudinal thickening is comprised of a wire.

23. A photobioreactor comprising:
a fluid-containing receptacle having opposing first and second outer side surfaces that are formed of a flexible transparent material; and
a rack supporting the receptacle, the rack comprising vertical support elements that are spaced apart along a center line, and that abut the first and second outer side surfaces of the receptacle such that at each location along the center line, only one support element abuts the receptacle.

24. The photobioreactor according to claim 23, wherein the support elements alternately abut the first and second side surfaces of the receptacle along the center line.

* * * * *